(12) United States Patent
Tsai et al.

(10) Patent No.: US 9,687,208 B2
(45) Date of Patent: Jun. 27, 2017

(54) METHOD AND SYSTEM FOR RECOGNIZING PHYSIOLOGICAL SOUND

(71) Applicant: IMEDIPLUS INC., Chupei (TW)

(72) Inventors: Kun-Hsi Tsai, Chupei (TW); Yu Tsao, Taipei (TW); Shih-Hsuan Ku, Chupei (TW); Tzu-Chen Liang, Chupei (TW); Yun-Fan Chang, Taipei (TW); Shih-I Yang, Chupei (TW)

(73) Assignee: IMEDI PLUS Inc., Hsinchu (TW)

( * ) Notice: Subject to any disclaimer, the term of this patent is extended or adjusted under 35 U.S.C. 154(b) by 0 days.

(21) Appl. No.: 14/729,423

(22) Filed: Jun. 3, 2015

(65) Prior Publication Data

US 2016/0354053 A1   Dec. 8, 2016

(51) Int. Cl.
| | |
|---|---|
| A61B 5/024 | (2006.01) |
| A61B 7/04 | (2006.01) |
| A61B 5/00 | (2006.01) |
| A61B 8/08 | (2006.01) |
| A61B 5/02 | (2006.01) |
| A61B 5/08 | (2006.01) |
| A61B 5/11 | (2006.01) |
| G06F 19/00 | (2011.01) |

(Continued)

(52) U.S. Cl.
CPC ............ *A61B 7/04* (2013.01); *A61B 5/02028* (2013.01); *A61B 5/0803* (2013.01); *A61B 5/1107* (2013.01); *A61B 5/4255* (2013.01); *A61B 5/7246* (2013.01); *A61B 5/7253* (2013.01); *A61B 5/7264* (2013.01); *A61B 5/7267* (2013.01); *A61B 5/7275* (2013.01); *A61B 5/7282* (2013.01); *A61B 7/003* (2013.01); *A61B 7/008* (2013.01); *A61B 8/0883* (2013.01); *A61B 8/0891* (2013.01); *A61B 8/5223* (2013.01); *G06F 19/345* (2013.01); *G06F 19/3431* (2013.01); *G06F 19/3481* (2013.01); *A61B 5/0205* (2013.01); *A61B 5/0428* (2013.01); *A61B 5/113* (2013.01); *A61B 2562/0204* (2013.01); *A61N 1/36578* (2013.01); *A61N 1/39* (2013.01)

(58) Field of Classification Search
None
See application file for complete search history.

(56) References Cited

U.S. PATENT DOCUMENTS

| | | | |
|---|---|---|---|
| 2012/0233168 A1* | 9/2012 | Terao | G06F 17/30705 707/738 |
| 2012/0242501 A1* | 9/2012 | Tran | A61B 5/0024 340/870.02 |

(Continued)

*Primary Examiner* — Erica Lee
(74) *Attorney, Agent, or Firm* — Steven Reiss

(57) ABSTRACT

A system for recognizing physiological sound comprises a receiving module, a feature extracting module, a classifier, and a comparing module. A method for recognizing physiological sound comprises receiving a physiological sound by the receiving module; extracting at least one feature from the physiological sound by the feature extraction module; classifying the at least one feature to identify at least one category by a classifier; and comparing the at least one category with a normal physiological sound and/or an abnormal physiological sound by the comparing module for evaluating a risk of disease. The method and system for recognizing physiological sound can precisely identify the specific physiological sound and exclude the noise.

17 Claims, 11 Drawing Sheets

(51) Int. Cl.
*A61B 7/00* (2006.01)
*A61N 1/39* (2006.01)
*A61B 5/0205* (2006.01)
*A61B 5/0428* (2006.01)
*A61B 5/113* (2006.01)
*A61N 1/365* (2006.01)

(56) References Cited

U.S. PATENT DOCUMENTS

| | | | |
|---|---|---|---|
| 2013/0237873 A1* | 9/2013 | Zhang | A61B 5/686 600/513 |
| 2015/0073306 A1* | 3/2015 | Abeyratne | A61B 7/003 600/586 |
| 2016/0322042 A1* | 11/2016 | Vlietinck | G10L 15/063 |

\* cited by examiner

METHOD AND SYSTEM FOR RECOGNIZING PHYSIOLOGICAL SOUND

BACKGROUND OF THE INVENTION

1. Field of the Invention

The present invention relates to method for recognizing physiological sound, particularly to a method for extracting and classifying the feature of the physiological sound. The present invention also relates to a system for recognizing physiological sound.

2. Description of the Prior Arts

Analysis of heart, lung, bowel and vascular disorders by means of noninvasive auscultation has long been a very useful tool for medical diagnosis of ailments. Conventional electronic stethoscopes were not invented until 1922. Modern electronic stethoscopes can improve sound quality and provide a visual indication of heart sounds, such as phonocardiogram (PCG). PCG and electrocardiogram (ECG) are applied in the basic examination for the heart. PCG could be obtained by recording the electric signals converted from mechanical vibration (collected via placing stethoscope in certain parts of the chest) by instrument. ECG could be obtained by placing electrodes on any two places of the heart and connecting two electrodes to the positive and negative poles of ECG machine to form leads and record the ECG voltage changes of the two places in the human body. ECG could be shown in ECG paper or monitor and further reflect the rhythms of beating heart as well as the weaker parts of myocardial muscles. The pitches and occurrence time of heart sounds follow certain regular patterns. The first heart sound (S1) and the second heart sound (S2) could be observed in a normal heart. The first heart sound occurs in the contraction period of the heart, which is caused by the blood flowing into great vessels during the contraction of ventricles (ventricle contracts and both mitral valve and tricuspid valve close). The first heart sound continues for relatively longer time and with low pitch. The second heart sound occurs in the relaxation period of heart, which is caused by the vibration of ventricular wall during ventricular relaxation (aortic and pulmonary valves close and atrioventricular valve opens to allow blood flowing from atrium to ventricle). The duration of the second heart sound is shorter. Clinically, abnormal third and fourth heart sounds sometimes would be detected. The third heart sound shows low frequency and amplitude, which is caused by the vibration of ventricular wall. The fourth heart sound is caused by the vibration of ventricular wall during atrial contraction owing to blood flow rapidly entering ventricle.

Many heart diseases could be effectively diagnosed through auscultation. In some deadly heart diseases (such as heart valve dysfunction, heart failure, etc.), cardiac auscultation has already become the most successful, reliable, and inexpensive method in early diagnosis. However, the correctness of cardiac auscultation is closely related to the experiences of doctors. Also, some diseases show obvious occurrence patterns (for example, during S1 and S2 or after S2, etc.). Therefore, how to automatically detect and preliminarily judge the occurring time of S1 and S2 has already become an important issue. This issue could effectively help doctors to confirm the occurrences of diseases preliminarily. In normal situation, the time order of S1 and S2 could serve as the materials for making judgments. Nevertheless, time order is no longer reliable under the circumstances of arrhythmia. If voiceprint comparison for S1 and S2 is available, the judgment on the case of arrhythmia could be improved in quality. Researches about heart sound detection could be divided into two categories: ECG signal dependent and ECG signal independent. ECG signal dependent researches include ECG-based detections on instantaneous energy (Malarvili et al., 2003) and detection on QRS wave group and T wave (El-Segaier et al., 2005). Nonetheless, in low-quality ECG signals, it is not always possible to clearly detect T wave. Under such situation, S2 could be classified using unsupervised classifier (Carvalho et al., 2005), although such method should consider hardware equipment and the comfort of examinees. ECG-independent methods could be divided into unsupervised and supervised methods. Unsupervised methods include using normalized average Shannon energy (Liang et al., 1997) and high frequency-based methods (Kumar et al., 2006) for wavelet decomposition. Supervised methods include neural network classifier (Hebden et al., 1996) and decision making trees (Stasis et al., 1996) used for classification. In addition, the most advanced method used in recent years is to detect according to the features of the regular intervals between S1 and S2. Generally, average heart rate (Olmez et al., 2003, Kumar et al., 2006) would be assumed in research. However, such assumption is not applicable in the heart sound of arrhythmia patients.

It is relatively difficult to simultaneously and synchronously record and analyze ECG and PCG in actual clinical cases. Also, when PEA occurs, ECG cannot determine that the heart rate has stopped due to the maintenance of electrical activity. Thus, how to make diagnosis according to solely PCG became an important and mainstream research topic. Mainstream detection methods usually include the time interval features of S1 and S2. But this feature would become unreliable under the situation of arrhythmia and highly decrease the correctness of detection. Therefore, the disadvantages in prior arts should be resolved.

SUMMARY OF THE INVENTION

According to the above description, the objective of the present invention is to provide a system for recognizing physiological sound, comprising a receiving module, a feature extracting module, and a classifier. The receiving module is configured to receive a physiological sound; the feature extracting module is configured to extract at least one feature from the physiological sound; the classifier is configured to classify the at least one feature to identify at least one category.

Preferably, the receiving module is a physiological recording device converting an analog signal of the physiological sound into a digital signal of the physiological sound.

More preferably, the physiological recording device is an electronic stethoscope.

Preferably, the feature extracting module comprises a voice activity detector (VAD) module and a Mel-frequency cepstrum coefficients (MFCC) module. The VAD module is configured to detect at least one segment from the physiological sound; the MFCC module is configured to transfer the at least one segment to at least one MFCC feature vector.

More preferably, the system further comprises a K-means algorithm module configured to find at least one representative data point from the at least one MFCC feature vector.

Preferably, the classifier includes a supervised classifier.

More preferably, the supervised classifier includes a K-nearest neighbor (KNN) module, a Gaussian mixture model (GMM) module, a support vector machine (SVM) module, or a deep neural network (DNN) module.

Preferably, the physiological sound includes heart sound, lung sound, bowel sound, vascular sound, tracheal breath sound, bronchioles breath sound or extremities sound.

More preferably, the heart sound comprises first heart sound (S1), second heart sound (S2) or a combination thereof.

Preferably, the system further comprises a comparing module configured to compare the at least one category with a normal physiological sound and/or an abnormal physiological sound for evaluating a risk of disease.

Preferably, the system further comprises an automated external defibrillator, a Holter monitor, a cardiopulmonary resuscitation (CPR) machine, a pacemaker, an implantable cardioverter defibrillator (ICD), an electrocardiogram (EKG), or an ultrasonic wave device. When the system identifies that S1 and S2 are in non-critical condition, the system can be incorporated with heart rate detection devices. When the system identifies that S1 and S2 are on critical condition, the system can differentiate between pulse status and pulselessness in order to accurately determine which device should be used.

In one another aspect, the present invention also provides a method for recognizing physiological sound by the system as above mentioned, comprising receiving a physiological sound by the receiving module; extracting at least one feature from the physiological sound by the feature extraction module; and classifying the at least one feature to identify the at least one category by the classifier.

Preferably, extracting at least one feature from the physiological sound comprises: detecting at least one segment from the physiological sound by the VAD module; and transferring the at least one segment to the at least one MFCC feature vector by the MFCC module.

More preferably, the method further comprises: finding at least one representative data point from the at least one MFCC feature vector by the K-means algorithm module.

Preferably, the classifier includes a supervised classifier.

More preferably, the supervised the classifier includes the KNN module, the GMM module, the SVM module, or the DNN module.

Preferably, the physiological sound includes heart sound, lung sound, bowel sound, vascular sound, tracheal breath sound, bronchioles breath sound or extremities sound.

More preferably, the heart sound comprises S1, S2 or a combination thereof.

Preferably, the method further comprises: comparing the at least one category with a normal physiological sound and/or an abnormal physiological sound by the comparing module for evaluating a risk of disease.

The advantages are the method and the system for recognizing physiological sound of the present invention can precisely identify the specific physiological sound and exclude the noise.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
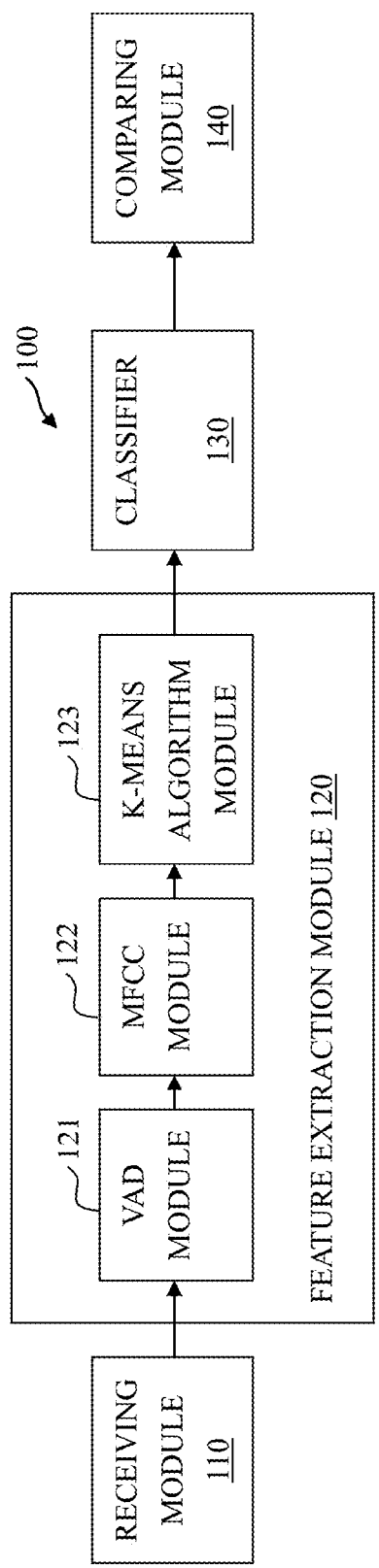
FIG. 1 shows a block diagram of the system for recognizing physiological sound of the present invention.
Figure 2:
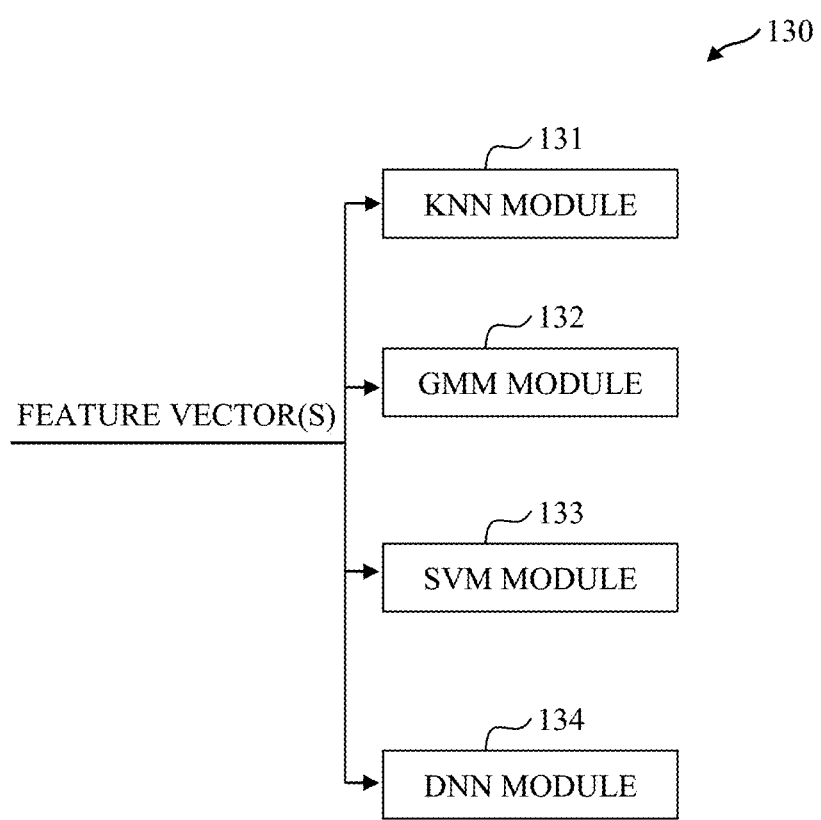
FIG. 2 shows the classifier comprising the KNN module, the GMM module, the SVM module, and the DNN module of the present invention.

The present invention provides a method and system for recognizing physiological sound. As shown in FIGS. 1 and 2, the system for recognizing physiological sound 100 comprises a receiving module 110, a feature extraction module 120, a classifier 130, and a comparing module 140. The feature extraction module 120 comprises a VAD module 121, an MFCC module 122, and a K-means algorithm module 123; the classifier 130 comprises a KNN module 131, a GMM module 132, an SVM module 133, or a DNN module 134.

Preparation 1 Feature Extraction (1) VAD Module 121

Figure 3:
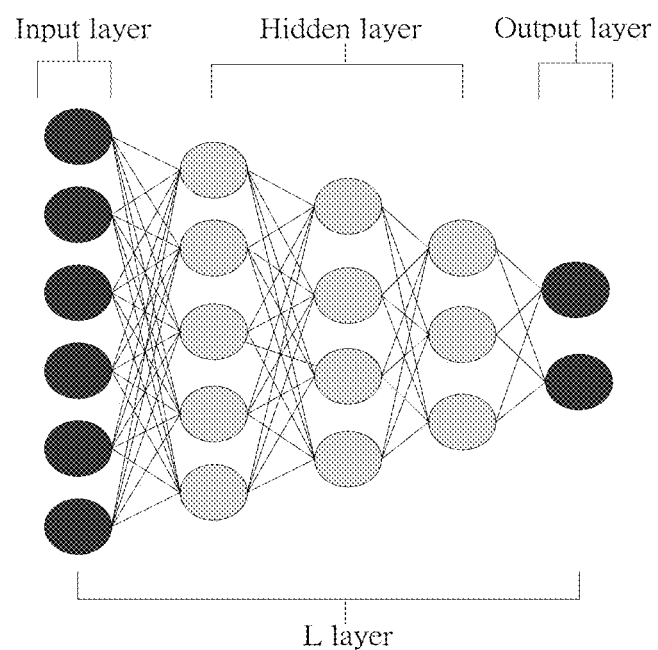
FIG. 3 is a DNN network model.

The VAD module 121 is also called Speech Activity Detection or Speech Detection and is usually used to determine whether a voice signal is processed by vocal voice processing technology. The main application of the VAD module 121 is in speech coding and speech recognition. The VAD module 121 is also usually used in the pretreatment before classification to increase recognition correctness of later investigations. The purpose for this pretreatment is to find out the position of S1 and S2 and further detect whether this segment of voice is S1 or S2. Ideally, heart sound signals received through a stethoscope are usually stronger than noises, so we could determine whether this segment is the heart sound we want according to voice energy differences. The processing results after the VAD module 121 treatment are shown in FIG. 3. Energy difference serves as the accordance for determining where the heart sounds are from.

First of all, the maximum standard deviation of each voice signal was calculated according to Formula (1).

$$\tau = \max_{m} \sqrt{\frac{\sum_{i=1}^{n}(x[n,m])^2 - \mu^2}{n}} \qquad \text{Formula (1)}$$

In Formula (1), m is sound frame and n is frequency domain. μ is average.

Then is the calculation for confirming whether each sound frame has heart sound in each segment of voice, as shown in Formula (2).

$$f_i = \begin{cases} 1, \text{ if } std_i > \tau - \alpha \text{ and } std_i > \beta \\ 0, \text{ else} \end{cases} \quad \text{Formula (2)}$$

$f_i$ is ith sound frame. 1 means heart sound and 0 means still sound. $std_i$ is the deviation for ith sound frame. α and β are parameters.

(2) MFCC Module 122

In general, humans show different perception sensitivity in different intervals of frequency domain. Under normal circumstance, low frequency shows higher resolution, which means smaller frequency difference could be detected in low frequency situation. Critical band phenomenon should also be considered. The critical band width is about 100 Hz below 1 kHz. When the frequency is higher than 1 kHz, the critical band width would show exponential increase. Thus, we could divide frequency bands in frequency domain according to the characteristics of human auditory. The frequency compositions in one frequency band are integrated into energy intensity. These frequency band intensities are then converted into cepstrum after the calculation of Discrete Cosine Transform (DCT), which is exactly Mel-Frequency Cepstrum (MFC). Since MFC is the parameter produced from the model for human auditory, MFC is successfully applied in speech recognition and classification. There are 6 sequential operations for the MFCC module 122: pre-emphasis, windowing, fast fourier transform (FFT), mel filtering, non-linear transformation and discrete cosine transform (DCT).

Generally, 13 dimensions of voice features could be obtained after the 6 steps described above, including 1 logarithmic energy parameter and 12 cepstrum parameters. Furthermore, differential cepstrum parameters are added to reveal how cepstrum parameters change with time. The meaning of differential cepstrum parameter is the slope of cepstrum parameter versus time, which means the dynamic change of cepstrum parameter. Hence, 39 dimensions of voice features could be obtained after adding the discussion about velocity and acceleration. The calculation methods are shown below.

$$vel[i, t] = \frac{\sum_{m=1}^{4} m \cdot [c[i, t+m] - c[i, t-m]]}{2 \sum_{m=1}^{4} m^2} \quad \text{Formula (3)}$$

$$acc[i, t] = \frac{\sum_{m=1}^{4} m \cdot [vel[i, t+m] - vel[i, t-m]]}{2 \sum_{m=1}^{4} m^2} \quad \text{Formula (4)}$$

c[i] is the ith dimension of cepstrum parameter and t is the time indicator for sound frame.

(3) K-Means Algorithm Module 123

The main goal of the K-means algorithm module 123 is to find out representative data points from huge amount of high dimensional data points. These data points could be called population centers. Data compression (using small number of data points to represent large amount of data to compress data) and classification (using small number of representative points to represent specific categories to lower data amount and calculation and avoid adverse effects brought by noises) are conducted on population centers. The calculation steps of algorithm are shown below.

A. Initialization: divide training materials randomly into K groups and arbitrarily select K values as the initial population center $y_k$. k=1, 2, ..., K B. Recursive Calculation:

a. Let each x find the nearest population center and make it belong to said population center. Calculate the distance between x and the population center to which x belongs.

$$k^* = \arg_k \min d(x, y_k), x \in C_{k^*} \quad \text{Formula (5)}$$

b. All of x belonging to $C_k$ forms a group. Calculate the population center $y_k$ again.

c. If the new groups of population centers are the same as the original population center set, the training is completed. Otherwise, new groups of populations replace the original population center groups. Step a is repeated to continue recursive calculations.

Preparation 2 Classifier (1) KNN Module 131

The basic concept behind the KNN module 131 is that "like attracts like". In other words, objects of the same type should gather together. In mathematical language, if objects of the same type could be represented by point in high dimension of space, the distances between these points should become closer. Therefore, while faced with a set of data in an unknown category, we only need to find out the nearest point in training data. By doing so, the categories of these data could be regarded as the same as the nearest point. The classification steps of the KNN module 131 is to categorize measurement data x to one of the C categories. The steps are described in detail as follows:

A. Determine which data x is used and find the nearest point number K. Use appropriate distance formula to calculate the distance.

B. When testing data x shows relatively higher similarities with certain category (among K category), x will be regarded as that category.

The pre-needed information for classifier is the nearest K number of point, selected distance calculation formula, and training data.

Assuming that our training set is paired as $(x_i, z_i)$, i=1, ..., n. $x_i$ is the ith vector for training data and $z_i$ is the corresponding classification index (For example, $z_i=j$ represents that ith training data vector is the sample for $\omega_d$ in jth category). The distance between testing data vector x and training data vector y is expressed as d(xy). In this study, Euclidean metric was used as the distance calculation method, which is shown in Formula (6).

$$d(x, y) = |x - y| = \sqrt{\sum_{i=1}^{d} (x_i - y_i)^2} \quad \text{Formula (6)}$$

(2) GMM Module 132

Gaussian Classifier is a common classifier, which applies Bayes' Theorem as fundamental concept. That is why Gaussian Classifier is also called Bayes' Classifier. The concepts of Gaussian Classifier is to utilize known categorized data to calculate probability distribution and find out the possibilities of unknown categories data in each possibility distribution of known category. The category shows the highest possibility would be chosen as the category of the unknown data. The average value and standard deviation serve as the two parameters that determine the whole model.

Single Gaussian distribution is to describe the distribution shape according to one average and one standard deviation. However, signals are usually distributed in a more complex manner. So, one Gaussian distribution is usually insufficient to approximate said signal. Gaussian mixture model is to involve multiple Gaussian distributions to approximate signals. As such, the distribution of the signals could be better approximated. Nevertheless, as the number of mixed Gaussian curves increases, the distribution shapes would become similar and the complexity would relatively increase.

Gaussian mixture model is composed of 3 items: mean vector $\mu_i$, covariance matrix $\Sigma_i$, and weighed value $\omega_i$. To show Gaussian model in a simplified way $\lambda$, the expression formula is shown as Formula (7).

$$\lambda = \{\omega_i, \mu_i, \Sigma_i\}, i=1,\ldots,K \qquad \text{Formula (7)}$$

The mixed probability density function of feature vector z could be expressed as $$p(z[n] \mid \lambda) = \sum_{i=1}^{K} \omega_i p_i(z[n]) \qquad \text{Formula (8)}$$

$p_i(z)$ is the ith Gaussian probability density function of feature vector z.

$$p_i(z[n]) = \frac{1}{(2\pi)^{d/2}|\Sigma_i|^{1/2}} \exp\left(-\frac{1}{2}(z[n]-\mu_i)^T \Sigma_i^{-1}(z[n]-\mu_i)\right) \qquad \text{Formula (9)}$$

Since the maximum probability value is 1, the weighed value $\omega_i$ of mixed probability density function in Gaussian mixture model must conform to the condition described in Formula (10).

$$\sum_{i=1}^{K} \omega_i = 1, \omega_i \geq 0, 1 \leq i \leq K \qquad \text{Formula (10)}$$

When there is/are N number of feature vector(s) z with dimension d, to train this training sample to be in line with Gaussian mixture model $\lambda$ is also to obtain the proper 3 parameters $\mu_i$, $\Sigma_i$, and $\omega_i$ (i=1, ..., k). The final goal is to allow trained model to fully represent the distribution of feature vector z, that is, to find a proper model parameter to allow feature vector z and Gaussian mixture model $\lambda$ to show the maximal similarity $p(z|\lambda)$, as shown in Formula (11).

$$p(z \mid \lambda) = \prod_{n=1}^{N} p(z_n \mid \lambda) \qquad \text{Formula (11)}$$

Since Formula (8) is a nonlinear equation, complex calculation is inevitable during solving. Generally, EM algorithm is applied to find out the optimal parameter in Gaussian mixture model.

(3) SVM Module 133

The SVM module 133 has been widely used in statistical classification and regression analysis. It has been proved by experiments that the SVM module 133 has strong classification capability. The central concept for the SVM module 133 is to reflect training data to high-dimensional feature plane and build up an optimal super plane (a plane in high dimension and with boundary at large intervals). Most of the SVMs mainly are applied in binary classification. It is also acceptable to combine multiple binary classifications to construct multi-category classification. The situations could be divided into linear data and non-linear data.

Assuming a set $\{xi, i=1, \ldots, n\}$ and the set is assigned to either the category of $\omega_1$ or $\omega_2$. The corresponding mark is noted as $y_i = \pm 1$. The goal is to find a super plane $g(x)$ ($g(x)=w^T x+w_0$) to allow all the points of $y_i=+1$ to fall in the side of $g(x)>0$. By doing so, the sign of $g(x)$ could serve as the accordance for distinguishing in the hope to find the plane that shows the largest distances to the two side borders, called the best super plane. To make the distance of $H_1$ and $H_2$ become the largest, it is essential to solve Formula (12).

$$\min\left\{\frac{1}{2}w^T w\right\} \qquad \text{Formula (12)}$$

Limitation is described in Formula (13)

$$y_i(w^T x_i + w_0) \geq 1, i=1,\ldots,n \qquad \text{Formula (13)}$$

When data is not linear and separable, kernel function is used as Formula (14), which projects data to higher dimension feature space.

$$k(x,y) = \langle \phi(x), \phi(y) \rangle \qquad \text{Formula (14)}$$

Common kernel function includes linear polynomial Gaussian radial basis function. Different kernel functions could be selected according to different classification characteristics. In this study, Gaussian radial basis function kernel is applied as kernel function, as shown in Formula (15).

$$K(x,y) = \exp(-\|x-y\|/2\sigma^2) \qquad \text{Formula (15)}$$

(4) DNN Module 134

Neural network (NN) is one mathematical model that mimics biological neural network structure and function to allow computer to undergo self-learning and deduce according to the rule of thumb, which makes neural network become more advantageous than logic inference calculus. Neural network algorithm has certain characteristics as follows: 1. parallel processing, 2. fault-tolerant, 3. combined memory, 4. solving optimal problems, 5. implementation of very-large-scale integration (VLSI), and 6. processing problems that are difficult for normal algorithm. So far, many scholars proposed different neural network models to solve different problems. Common neural network models include back-propagation network, Hopfield network and radial basis function network.

The operation of the DNN module 134 is to take output layer to serve as the input of the next hidden layer. The concept is to utilize the increase of hidden layer number to strengthen the system. FIG. 3 is the DNN module 134 having five layers. The relation between input layer and the output of 1st hidden layer is described as Formula (16).

$$a_2 = f(W_1 x) \qquad \text{Formula (16)}$$

x is the input and $W_1$ is the weight. $f$ is the activation function. Sigmoid function is used in this study. $a_2$ is the output of the second layer.

After the output of the first hidden layer is obtained, the relation is shown as Formula (17). L is a layer number of the DNN module 134.

$$a_{i+1} = f(W_i a_i), i = 2, L, L-1 \quad \text{Formula (17)}$$

Besides, since the initial value of the parameter would influence the calculation results, the DNN module 134 usually uses restricted Boltzmann machines (RBM) to conduct the prediction for initial parameter and uses back-propagation to adjust parameters, as shown in Formula (18).

$$J(a_L, y) = \text{loss}(a_L, y) \quad \text{Formula (18)}$$

In Formula (18), y is label and $a_L$ is the output of Lth layer. In this study, loss function applies softmax function. The detailed algorithm may refer to references (Bengio, 2009, Mohamed et al., 2013). Lastly, frequent use of dropout may avoid overtraining and obtain better efficiency.

Preparation 3 Evaluation Methods

The evaluation methods are performed by the comparing module 140. The evaluation methods used in pattern recognition and information retrieval usually use precision, recall and F-measure to serve as the standards for evaluating the system is good or bad (Martin et al., 1997). The four situations considered are shown in Table 1, and each of the definitions are shown as in Formulae (19) to (21).

TABLE 1

Objective assessment matrix

| | Actual Class(Observation) | |
|---|---|---|
| Predicted Class (Expectation) | tp(true positive) Correct result | fp(false positive) False Alarm Unexpected result |
| | fn(false negative) Missed Detection Missing result | tn(true negative) Correct absence of result |

$$\text{Precision} = \frac{tp}{tp + fp} \quad \text{Formula (19)}$$

$$\text{recall} = \frac{tp}{tp + fn} \quad \text{Formula (20)}$$

$$F = 2 \cdot \frac{\text{precision} \cdot \text{recall}}{\text{precision} + \text{recall}} \quad \text{Formula (21)}$$

F-measure is also called $F_1$ measure, which represents the equal weights of precision and recall. Recall is usually called true positive rate or sensitivity, and precision is called positive predictive value. In classification research, accuracy is usually used to serve as evaluation standards, and the definition of accuracy is shown in Formula (22).

$$\text{Accuracy} = \frac{tp + tn}{tp + tn + fp + fn} \quad \text{Formula (22)}$$

Example 1 Experimental Corpus and Experimental Steps for Heart Sounds

Figure 4:
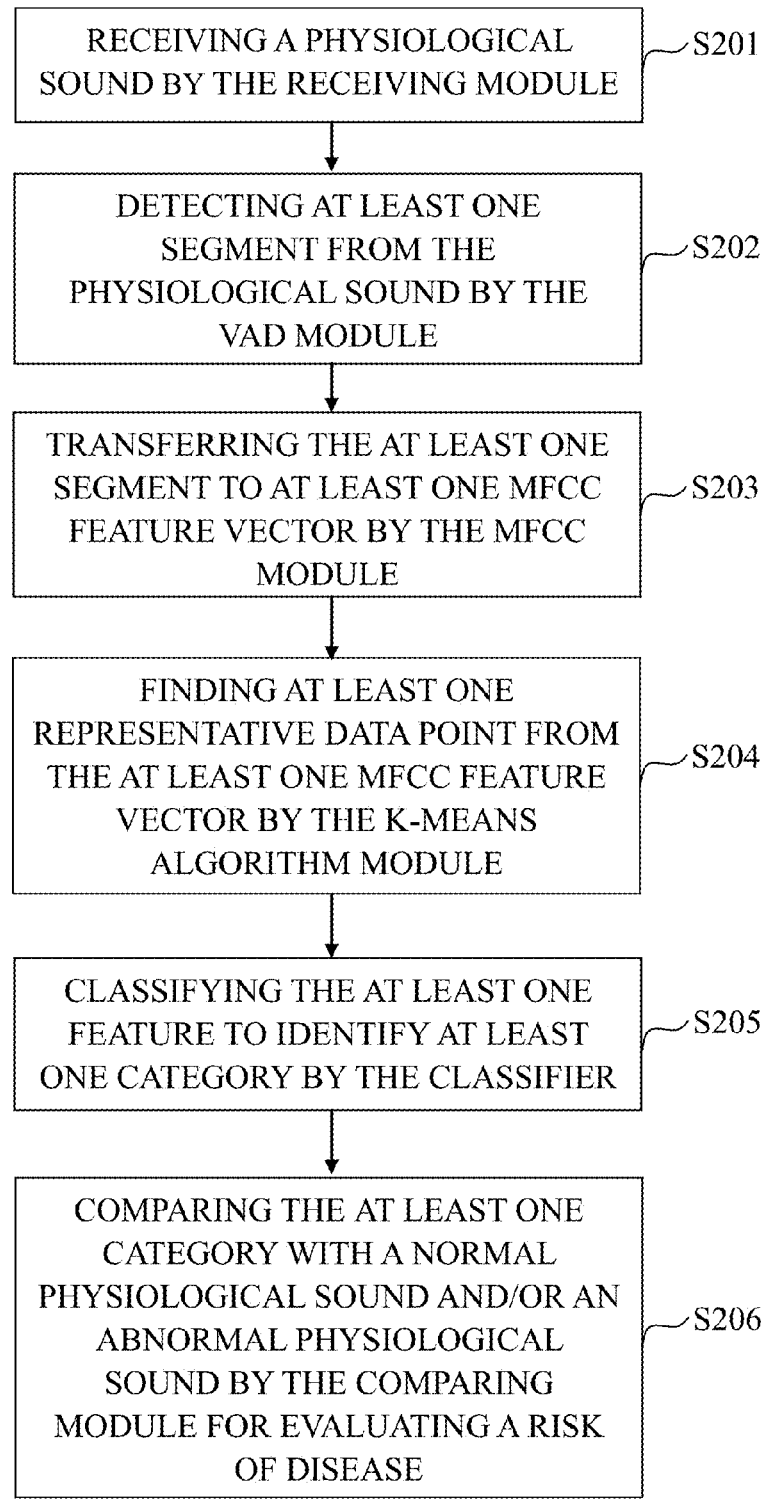
FIG. 4 shows a flow diagram illustrating the method for recognizing the physiological sound in FIG. 1; S201 to S206 represent Step 201 to Step 206 respectively.

The flow chart of the method for recognizing physiological sound is shown in FIGS. 1, 2 and 4. Step 201 is receiving a physiological sound by the receiving module 110. The place for receiving audios centralized on pulmonary valve auscultation area and second aortic valve auscultation area. The receiving module 110 is an electronic stethoscope, and the data used in this experiment is the actual voice data collected by the electronic stethoscope. The aim is to utilize heart sounds to find out the S1 and S2 audio clips. First of all, an analog microphone is used to record heart sounds and converted the recorded heart sounds into digital signals. Decoded by an audio codec, the digital audio signals are separated by two paths. One is to convert the filtered sounds into analog signals and deliver the analog signals through stethoscope ear tube. The other path is to store the non-processed digital sounds in the built-in memory. And these non-processed digital signals are used for analysis in this study.

Step 202 is deciding at least one segment from the physiological sound by the VAD module 121 of the feature extraction module 120. Because heart sounds centralize in low frequency, the sampling rate is set as 5 kHz. Training data 111 was recorded by 17 healthy people (11 males and 5 females). After extracting heart sounds S1 and S2 by artificial selection, totally 322 S1 and 313 S2 were obtained. Testing data 112 was recorded by 4 healthy people (3 males and 1 female). After processing VAD module 121 of the feature extraction module 120, 122 heart sounds were cut, wherein 66 heart sounds were S1 and 56 heart sounds were S2.

Step 203 is transferring the at least one segment to the at least one MFCC feature vector by the MFCC module 122 of the feature extraction module 120. MFCC feature vectors extracted by the MFCC module 122 were extended from 13 dimensions to 39 dimensions.

Step 204 is finding at least one representative data point from the at least one MFCC feature vector by the K-means algorithm module 123 of the feature extraction module 120. In each clip of heart sound, the K-means algorithm module 123 used 2 central vectors to represent the heart sound and noise parts.

Step 205 is classifying the at least one feature to identify at least one category by the classifier 130, wherein the classifier 130 comprises the KNN module 131, the GMM module 132, the SVM module 133, or the DNN module 134. Euclidean metric is the distance calculation method for the KNN module 131. In the SVM module 133, Gaussian radial basis function serves as the kernel function. S1 model and S2 model in the GMM module 132 each separately uses 8 mixed numbers. 3 hidden layers are set in the DNN module 134 and each layer has 100 neurons. Dropout was 70%.

Step 206 is comparing the at least one category with a normal physiological sound and/or an abnormal physiological sound by the comparing module 140 for evaluating a risk of disease. The normal heart sounds or abnormal heart sounds are recorded by the receiving module 110. After extracting heart sounds S1 and S2 by artificial selection, heart sounds S1 and S2 are trained to be training data.

Example 2 The Accuracy Result of Heart Sounds by Different Classifiers

Figure 5:
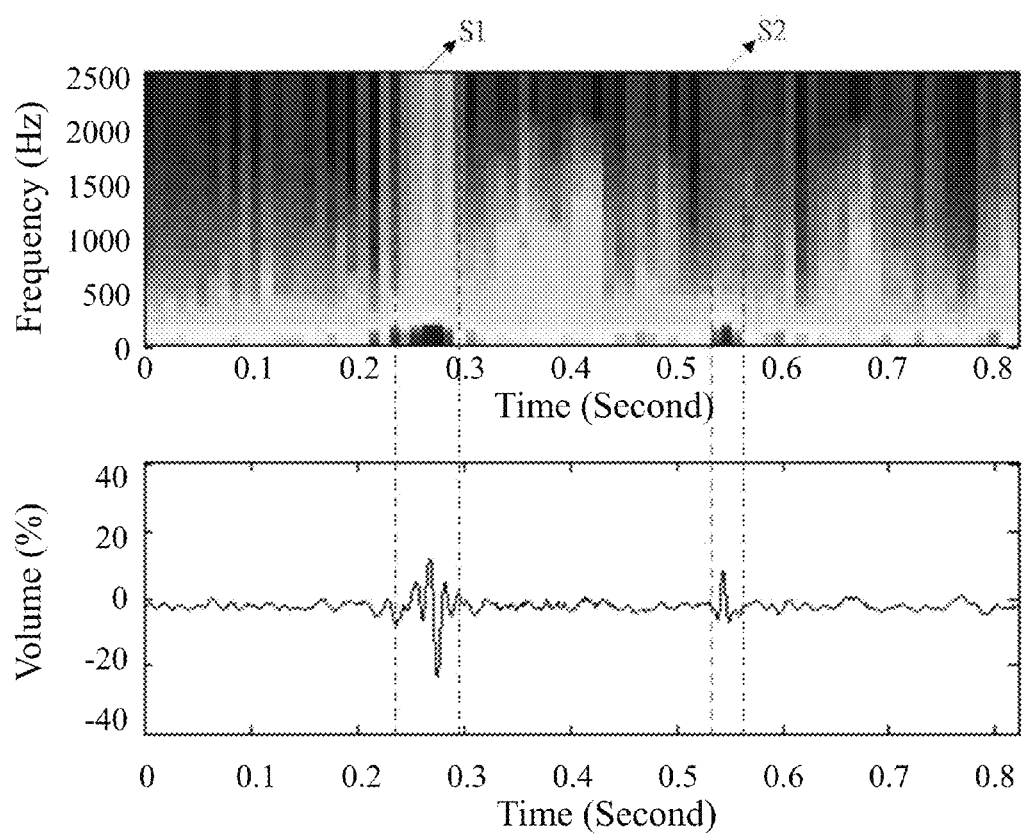
FIG. 5 is a spectrum (upper portion) and wave pattern (lower portion) map of S1 and S2 of the present invention.

In MFCC feature extraction of training data, the S1 and S2 spectrum and wave pattern map were observed and shown in FIG. 5. First, the frequency of heart sounds mainly concentrated in low frequency parts, which is highly different from voices concentrating below 8 k Hz. Therefore, sampling was adjusted to 5 k Hz. The baseband of heart sound is about 15 ms, so the frame size was set as 15 ms, with 10 ms overlapped. After adjusting the parameters of the VAD module 121 as the α and β shown in Formula (2), audio files cut manually served as goal to match the testing data processed by the VAD module 121 with training data.

In classifier part, the KNN module 131, the GMM module 132, the SVM module 133 and the DNN module 134 were used. However, the idea for using the KNN module 131 was relatively simpler, which merely used features to serve as the judgment standard for distances. The GMM module 132 was generation model. Each category was trained under Gaussian model separately. The possibility of testing data in individual model was also calculated. The SVM module 133 was to use linear or nonlinear (reflection) methods to classify training data to obtain the training model. Testing data then were introduced into model to obtain detection results. Finally, the DNN module 134 was the state-of-the-art identification method in recent years, which mimics the multiple layers of learning in human brains to obtain the training model. After introducing testing data, the detection results could be obtained.

TABLE 2

KNN experimental result

|  | Precision | Recall | F-measure | Accuracy |
|---|---|---|---|---|
| S1 | 85% | 77.3% | 81% | — |
| S2 | 75.8% | 83.9% | 79.7% | — |
| Average | — | — | — | 80.3% |

TABLE 3

GMM experimental result

|  | Precision | Recall | F-measure | Accuracy |
|---|---|---|---|---|
| S1 | 89.2% | 87.9% | 88.6% | — |
| S2 | 86% | 87.5% | 86.7% | — |
| Average | — | — | — | 87.7% |

TABLE 4

SVM experiment result

|  | Precision | Recall | F-measure | Accuracy |
|---|---|---|---|---|
| S1 | 96.7% | 89.4% | 92.9% | — |
| S2 | 88.5% | 96.4% | 92.3% | — |
| Average | — | — | — | 92.6% |

TABLE 5

DNN experiment result

|  | Precision | Recall | F-measure | Accuracy |
|---|---|---|---|---|
| S1 | 96.8% | 90.9% | 93.8% | — |
| S2 | 90% | 96.4% | 93.1% | — |
| Average | — | — | — | 93.4% |

Figure 6:
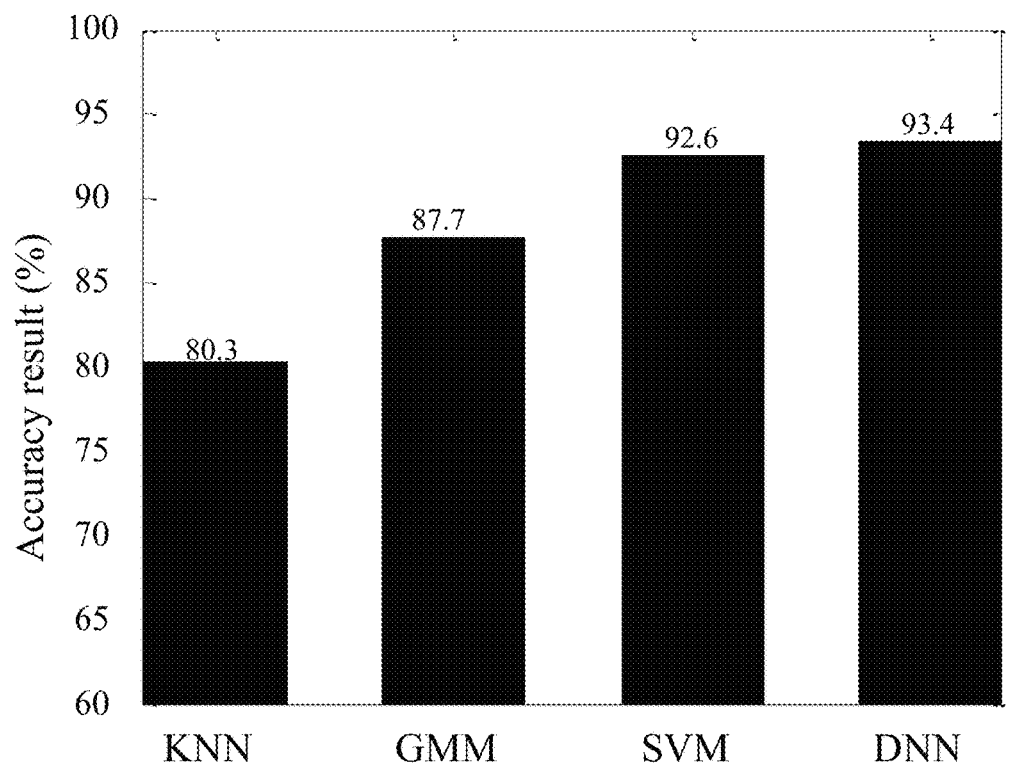
FIG. 6 shows accuracy results of heart sound with classifiers KNN module, GMM module, SVM module, and DNN module of the present invention.

From Tables 2 to 5 and FIG. 6 were the experiment results for the detections of S1 and S2 by using the proposed systematic structure. From the experiment results, the SVM module 133 and the DNN module 134 both showed very high recognition rate. The DNN module 134 accuracy could reach 93.4%. S1 owned higher F-measures in four kinds of classifiers.

Example 3 Identifying Regular Heart Sounds and Irregular Heart Sound

Figure 7:
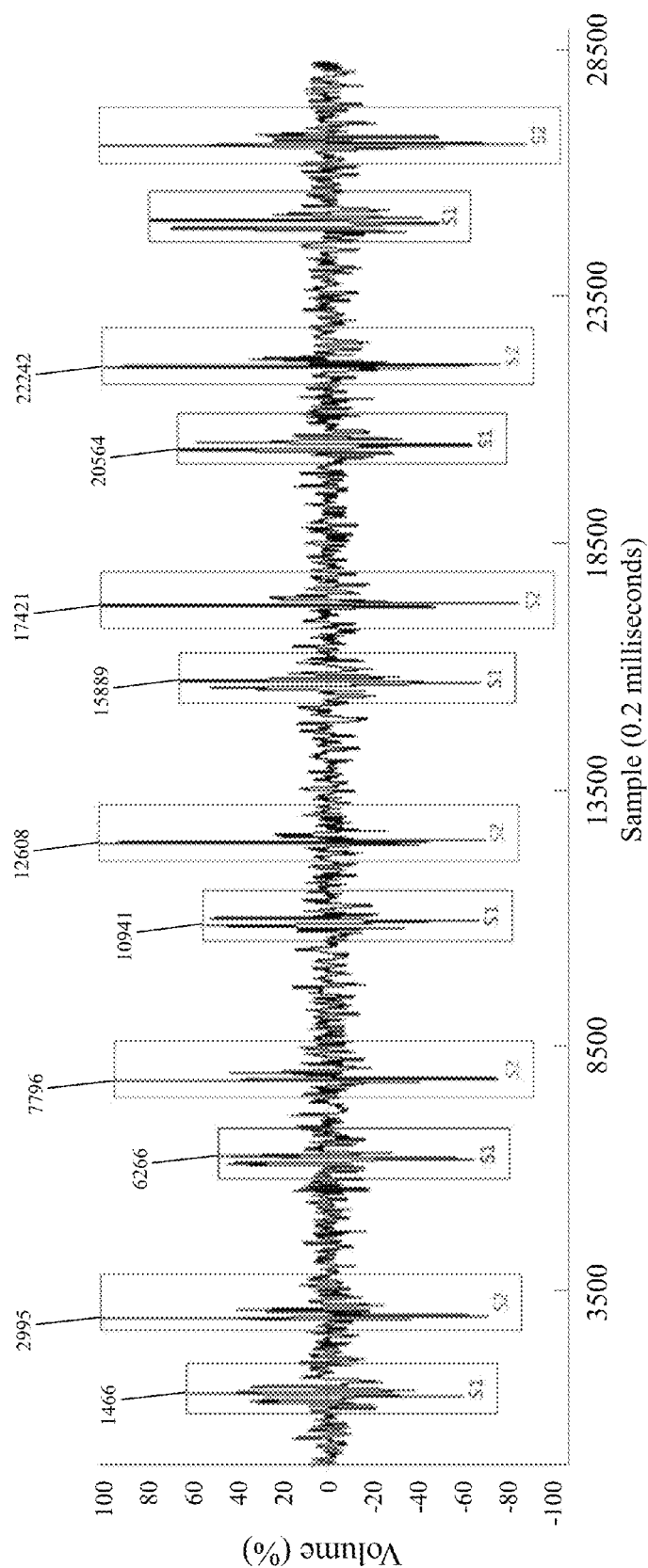
FIG. 7 shows segments (solid square lines) processed from energy differences of regular heart sounds by the VAD module.

To evaluate the difference between regular and irregular heart sounds, as shown in FIG. 7, three pairs of regular heart sounds S1 and three pairs of regular heart sounds S2 were recorded. Using five thousand (5 K) sampling rate as the record factor, and 5 K sampling rate was 0.2 milliseconds per sample. Each sample of S1 were respectively 1466, 6266, 10941, 15889, and 20564, and each sample of S2 were respectively 2995, 7796, 12608, 17421, and 22242. First heart rate of S1 was 60/[(|6266−1466|)×0.2×0.001]=62.5 beats per minute (BPM), and second heart rate of S1 was 64.2 BPM. The modulus difference between first and second heart rates was 1.7 (64.2 BPM−62.5 BPM) which was smaller than 5% of the first heart rate 3.125 (62.5 BPM× 5%).

Figure 8:
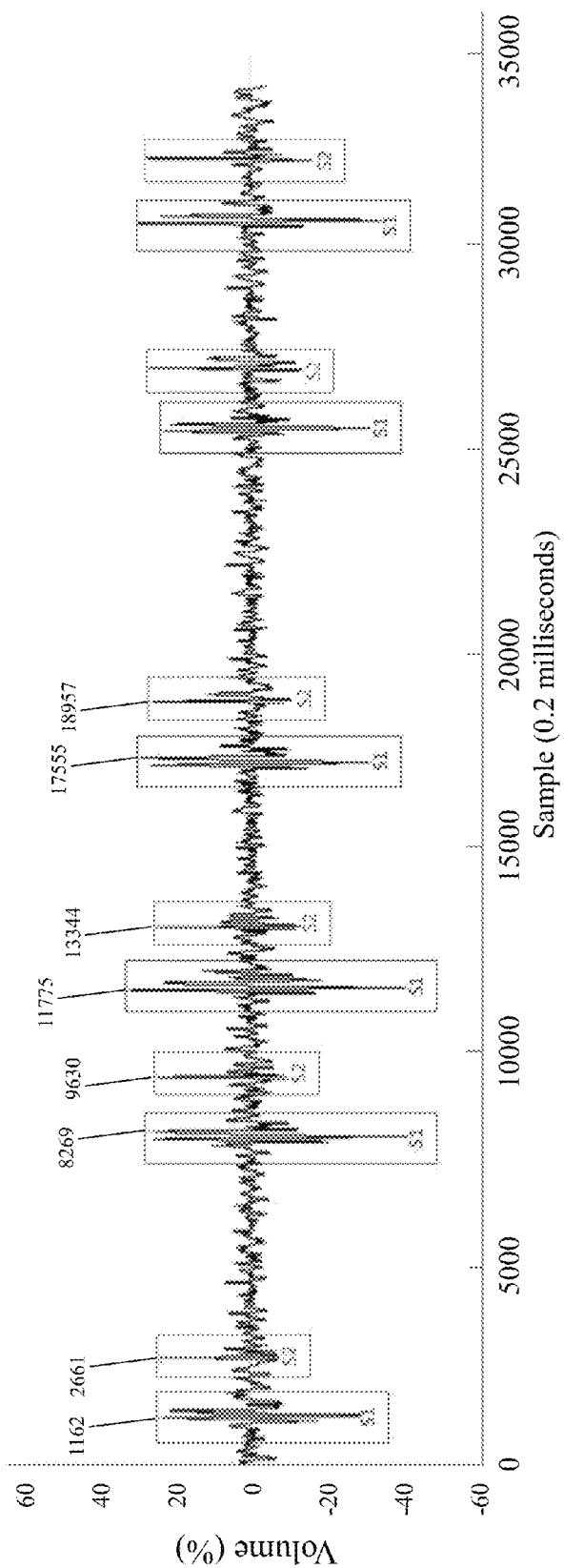
FIG. 8 shows segments (solid square lines) processed from energy differences of irregular heart sounds by the VAD module.

On the contrary, as shown in FIG. 8, three pairs of irregular heart sounds S1 and three pairs of irregular heart sounds S2 were recorded. Each sample of S1 were respectively 1162, 8269, 11775, and 17555, and each sample of S2 were respectively 2661, 9630, 13344, and 18957. Second heart rate of S1 was 42.8 BPM, and third heart rate of S1 was 51.9 BPM. The modulus difference between second and third heart rates was 9.1, which was larger than 5% of the second heart rate 2.14.

As shown in FIG. 1, the regular and irregular heart sounds were received by the receiving module 110 and two segments of each pair of S1 and S2 were detected by VAD module 121 of the feature extraction module 120, further calculating each heart rate and regularity. The modulus of differences between two heart rates is smaller than 5% of the prior heart rate, the heart rate is regular, and the modulus of differences between two heart rates is larger than 5% of the prior heart rate, the heart rate is irregular. The above method can identify the regular and irregular heart rate within two heart rate cycles.

As shown in FIGS. 1 and 2, the method combines the DNN module 134 voiceprint analysis and the VAD module 121, the MFCC module 122 to detect heart sounds S1 and S2. Because this method and system do not need to rely on the time interval information of S1 and S2, Arrhythmia problems could be effectively solved. The K-means algorithm module 123 is then used to represent heart sounds and noises. Simultaneously comparing precision, recall, F-measure and accuracy usually used in classification, the experiment results showed that both S1 and S2 showed excellent detection results in each experiment and S1 showed higher correction rate.

In actual clinical use, the concept that S1 and S2 appear in pair or individually could be introduced in extracting heart sound with the VAD module 121. Then, the characteristics of S1 to have better recognition rate could be utilized to obtain S2 according to the order detections. Also, the third heart sound (S3) and the fourth heart sound (S4) are the same concept and could be recognized by using the present invention as well.

Example 4 Identifying Regular and Irregular Lung Sounds

Figure 9:
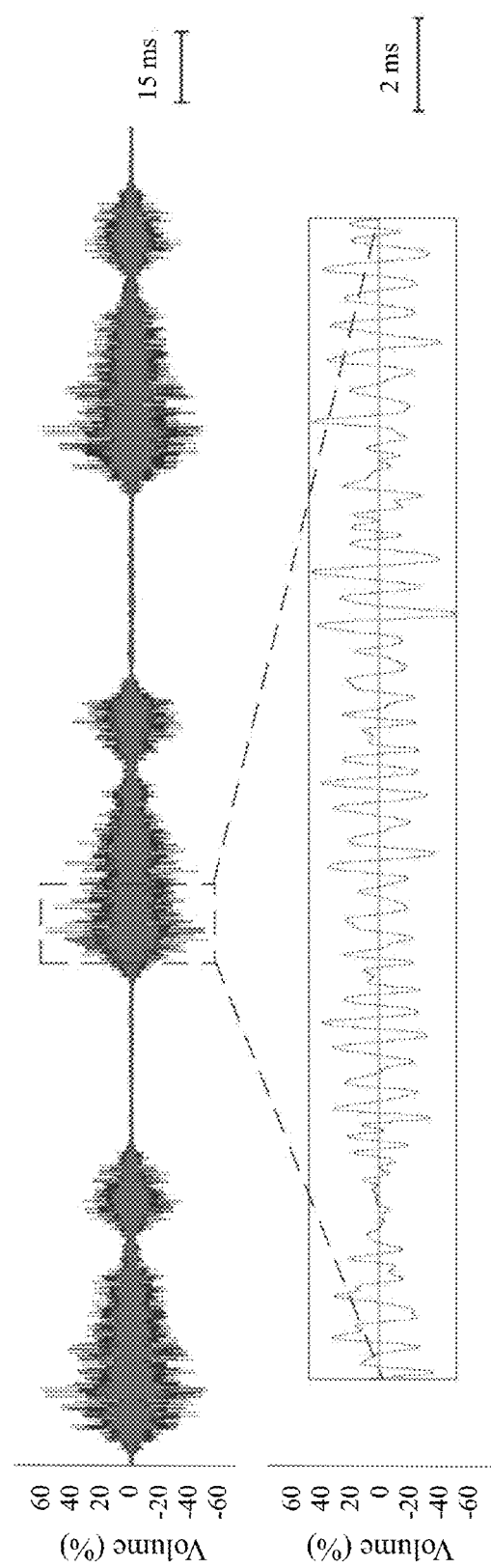
FIG. 9 shows segments (solid square line) processed from energy differences of normal lung sounds by the VAD module.
Figure 10:
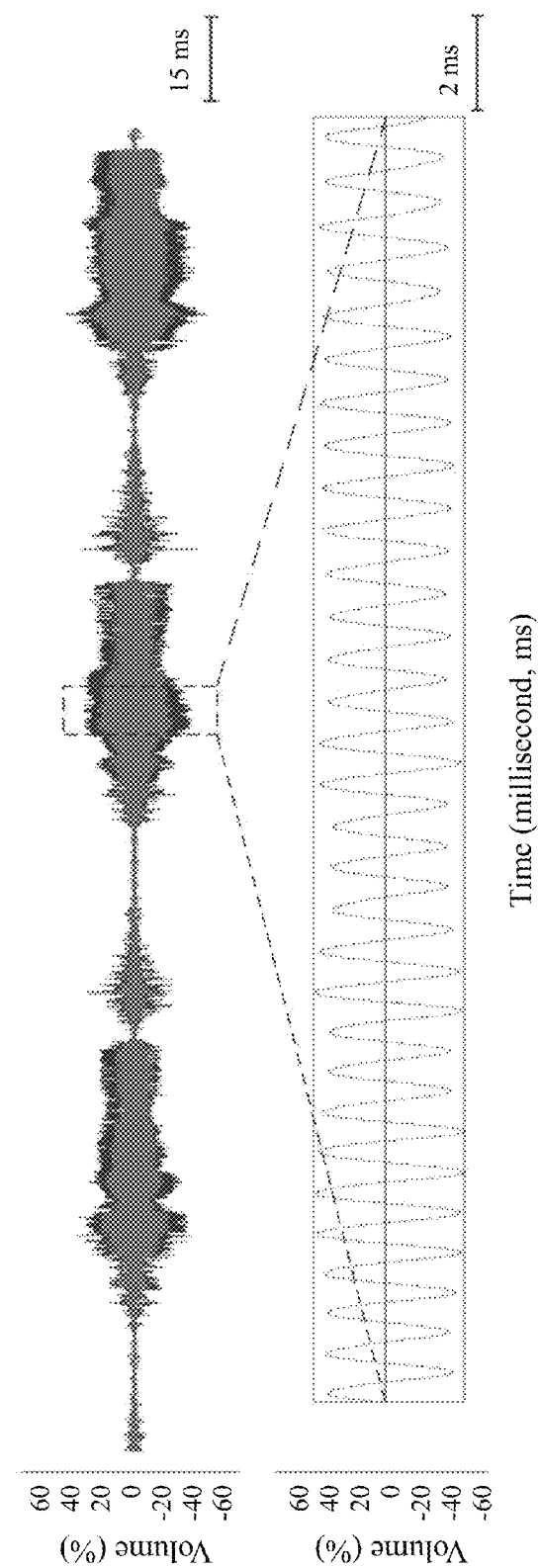
FIG. 10 shows segments (solid square line) processed from energy differences of wheezing lung by the VAD module.
Figure 11:
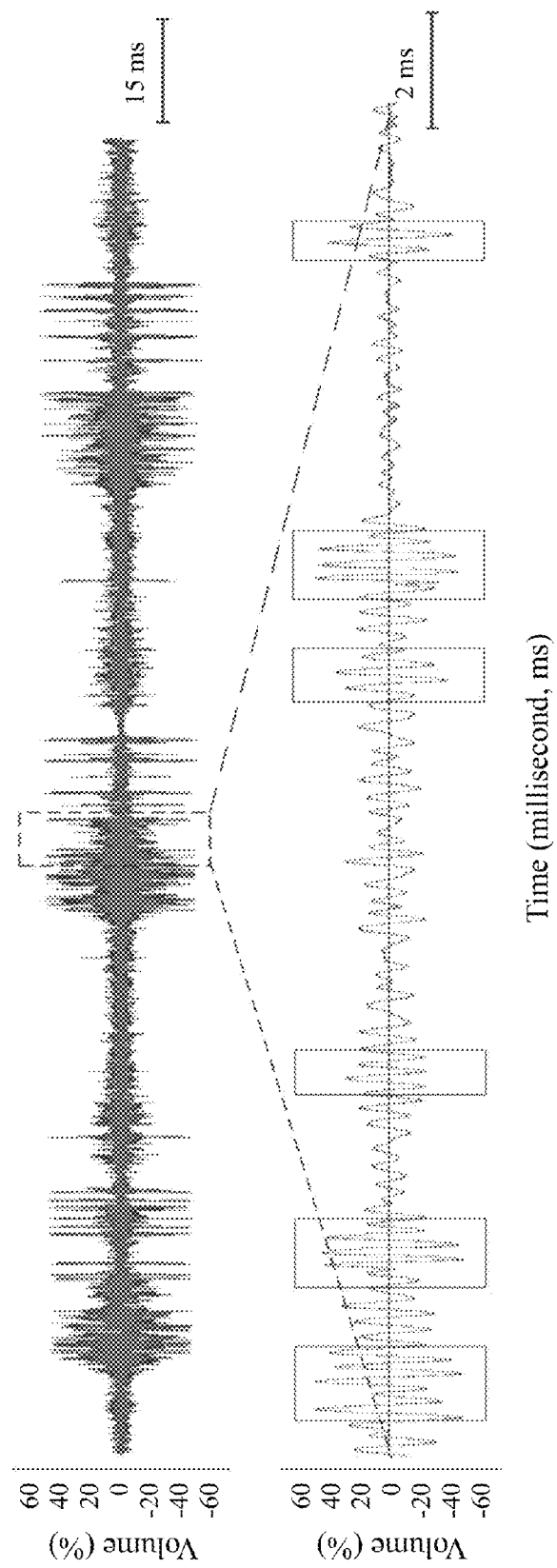
FIG. 11 shows segments (solid square lines) processed from energy differences of crackling lung sounds into energy differences by the VAD module.

As shown in FIGS. 1 and 4, the same steps were processed to identify regular and irregular lung sounds. The place for receiving audios was on the sixth intercostal space of the left chest area. The key step to identify different physiological sounds is detecting the segment of the physiological sounds by the VAD module 121 of the feature extraction module 120 because the different physiological sounds have their own segments. As shown in FIG. 9, energy differences of normal lung sounds were processed by the VAD module 121 into segments. As shown in FIGS. 1 and 10, energy differences of wheezing lung were processed by the VAD module 121 into segments. A wheeze (formally called "sibilant rhonchi" in medical terminology) is a continuous, coarse, whistling sound produced in the respiratory airways during breathing. Wheezing is commonly experienced by persons with asthma attacks. As shown in FIGS. 1 and 11, energy difference of crackling lung sounds were processed by the VAD module 121 into segments. Crackles are caused by the "popping open" of small airways and alveoli collapsed by fluid, exudate, or lack of aeration during expiration. Crackles can be heard in patients with pneumonia, or pulmonary edema.

Even though numerous characteristics and advantages of the present invention have been set forth in the foregoing description, together with details of the structure and features of the invention, the disclosure is illustrative only. Changes may be made in the details, especially using the system or the method for recognizing physiological sound such as the bowel sound, vascular sound, tracheal breath sound, bronchioles breath sound or extremities sound also within the principles of the invention to the full extent indicated by the broad general meaning of the terms in which the appended claims are expressed.

What is claimed is:

1. A system for recognizing physiological sound, comprising:
   a receiving module configured to receive a physiological sound;
   a feature extracting module configured to extract at least one feature from the physiological sound; and
   a classifier configured to classify the at least one feature to identify at least one category;
   wherein the feature extracting module comprises a voice activity detector (VAD) module configured to detect at least one segment from the physiological sound, a Mel-frequency cepstrum coefficients (MFCC) module configured to transfer the at least one segment to at least one MFCC feature vector, and a K-means algorithm module configured to find at least one representative data point from the at least one MFCC feature vector, wherein the at least one segment from the physiological sound comprises a first heart sound or a second heart sound, the feature extracting module is capable of calculating heart rates of the first heart sound or the second heart sound and calculating a modulus of differences between two adjacent heart rates, the classifier is configured to classify the at least one feature based on the modulus of differences between two adjacent heart rates to identify at least one category.

2. The system for recognizing physiological sound according to claim 1, wherein the receiving module is a physiological recording device converting an analog signal of the physiological sound into a digital signal of the physiological sound.

3. The system for recognizing physiological sound according to claim 2, wherein the physiological recording device is an electronic stethoscope.

4. The system for recognizing physiological sound according to claim 1, wherein the classifier includes a K-nearest neighbor (KNN) module, a Gaussian mixture model (GMM) module, a support vector machine (SVM) module.

5. The system for recognizing physiological sound according to claim 1, wherein the system further comprises:
   a comparing module configured to compare the at least one category with a normal physiological sound and/or an abnormal physiological sound for evaluating a risk of disease.

6. The system for recognizing physiological sound according to claim 1, wherein the system further comprises an automated external defibrillator, a Holter monitor, a Cardiopulmonary Resuscitation (CPR) machine, a pacemaker, an implantable cardioverter defibrillator (ICD), an electrocardiogram (EKG), or an ultrasonic wave device.

7. The system for recognizing physiological sound according to claim 1, wherein the classifier comprises a deep neural network (DNN) module.

8. The system for recognizing physiological sound according to claim 7, wherein the DNN module comprises three hidden layers, and each hidden layer comprises 100 neurons.

9. The system for recognizing physiological sound according to claim 1, wherein the classifier is configured to identify regular heart sounds or irregular heart sound by comparing the modulus to 5% of a prior heart rate of the two adjacent heart rates, the regular heart sounds are identified when the modulus is smaller than 5% of a prior heart rate of the two adjacent heart rates, and the irregular heart sounds are identified when the modulus is higher than 5% of a prior heart rate of the two adjacent heart rates.

10. The system for recognizing physiological sound according to claim 1, wherein the voice activity detector (VAD) module is configured for detecting the at least one segment from the physiological sound based on sound energy differences.

11. A method for recognizing physiological sound, comprising:
    providing a receiving module, a feature extracting module, and a classifier, wherein the feature extracting module comprises a voice activity detector (VAD) module, a Mel-frequency cepstrum coefficients (MFCC) module, and a K-means algorithm module;
    receiving a physiological sound by the receiving module;
    extracting at least one feature from the physiological sound by the feature extracting module; and
    classifying the at least one feature to identify at least one category by the classifier;
    wherein the extracting at least one feature from the physiological sound by the feature extracting module comprises:
    detecting at least one segment from the physiological sound by the VAD module;
    transferring the at least one segment to at least one MFCC feature vector by the MFCC module;
    finding at least one representative data point from the at least one MFCC feature vector by the K-means algorithm module;
    wherein the at least one segment from the physiological sound comprises a first heart sound or a second heart sound, the feature extracting module calculates heart rates of the first heart sound or the second heart sound and calculates a modulus of differences between two adjacent heart rates, and the classifier classifies the at least one feature based on the modulus of differences between two adjacent heart rates to identify at least one category.

12. The method for recognizing physiological sound according to claim 11, wherein the classifier includes a KNN module, a GMM module, an SVM module.

13. The method for recognizing physiological sound according to claim 11, wherein the method further comprises:
  comparing the at least one category with a normal physiological sound and/or an abnormal physiological sound by a comparing module for evaluating a risk of disease.

14. The method for recognizing physiological sound according to claim 11, wherein the classifier comprises a deep neural network (DNN) module.

15. The method for recognizing physiological sound according to claim 14, wherein the DNN module comprises three hidden layers, and each hidden layer comprises 100 neurons.

16. The method for recognizing physiological sound according to claim 11, wherein the heart rates are identified to be regular heart sounds or irregular heart sound by comparing the modulus to 5% of a prior heart rate of the two adjacent heart rates, the regular heart sounds are identified when the modulus is smaller than 5% of a prior heart rate of the two adjacent heart rates, and the irregular heart sounds are identified when the modulus is higher than 5% of a prior heart rate of the two adjacent heart rates.

17. The method for recognizing physiological sound according to claim 11, wherein the voice activity detector (VAD) module is configured for detecting the at least one segment from the physiological sound based on sound energy differences.

* * * * *